United States Patent [19]

Barsomian et al.

[11] Patent Number: 4,999,293
[45] Date of Patent: Mar. 12, 1991

[54] METHOD FOR PRODUCING THE HHAI RESTRICTION ENDONUCLEASE AND METHYLASE

[75] Inventors: Janet M. Barsomian, Georgetown; Geoffrey G. Wilson, Boxford, both of Mass.

[73] Assignee: New England Biolabs, Inc., Beverly, Mass.

[21] Appl. No.: 134,237

[22] Filed: Dec. 17, 1987

[51] Int. Cl.$^5$ .................... C12N 15/52; C12N 9/22; C12N 1/21
[52] U.S. Cl. ................... 435/172.3; 435/199; 435/252.33; 435/320.1; 536/27; 935/29; 935/73; 935/80
[58] Field of Search ............. 435/172.3, 199, 320, 435/252.33; 935/29, 73, 80, 82; 536/27

[56] References Cited

FOREIGN PATENT DOCUMENTS 0193413 3/1986 European Pat. Off. .
0248678 9/1987 European Pat. Off. .

OTHER PUBLICATIONS

Lunnen, K. D., et al. (1988), Gene 74, 25–32.
Wilson, G. G. (1988), Trends in Genetics 4(11), 314–318.
Wilson, G. G. (1988), Gene 74, 281–289.
Greene, P. J., et al. (1981), J. Biol. Chem. 256(5), 2143–2153.
Newman, A. K., et al. (1981), J. Biol. Chem. 256(5), 2131–2139.
Schoner, B., et al. (1983), Gene 24, 227–236.
Walder, R. Y., et al. (1984), J. Biol. Chem., 259(12), 8015–8026.
Mann et al, Gene 3: 97–112 (1978).
Kosykh et al., Molec Gen. Genet. 178:717–718 (1980).
Walder et al., Proc. Nat. Acad. Sci. U.S.A. 78 1503–1507 (1981).
Bougueleret et al., Nucleic Acids Res. 12:3659–3676, (1984).
Gingeras and Brooks, Proc. Natl. Acad. Sci. U.S.A. 80:402–406, (1983).
Theriault and Roy, Gene 19:355–359 (1982).
Blumenthal et al., J. Bacteriol. 164:501–509 (1985).
Kiss et al., Nucleic Acids Res. 13:6403–6421 (1985).
Szomolanyi et al., Gene 10:219–225 (1980).
Janulaitis et al., Gene 20:197–204 (1982).
Kiss and Baldauf, Gene 21:111–119 (1983).
Walder et al., J. Biol. Chem. 258:1235–1241 (1983).
Raleigh and Wilson, Proc. Natl. Acad. Sci. U.S.A. 83:9070–9074 (1986).
Roberts et al., J. Mol. Biol. 103:199–208 (1976).
Caserta et al., J. Biol. Chem. 262:4770–4777 (1987).
Birnboin and Doly, Nucleic Acids Res. 7:1513 (1979).

*Primary Examiner*—Elizabeth C. Weimar
*Assistant Examiner*—Charles L. Patterson, Jr.
*Attorney, Agent, or Firm*—Gregory D. Williams; David G. Conlin

[57] ABSTRACT

The present invention is directed to a method for cloning and producing the HhaI restriction endonuclease by (1) introducing the restriction endonuclease gene from *Haemophilus haemolyticus* ATCC 10014 into a host whereby the restriction gene is expressed; (2) fermenting the host which contains the vector encoding and expressing the HhaI restriction endonuclease, and (3) purifying the HhaI restriction endonuclease from the fermented host which contains the vector encoding and expressing the HhaI restriction endonuclease activity.

10 Claims, 3 Drawing Sheets

*Other HindIII sites are present but have not been mapped.

METHOD FOR PRODUCING THE HHAI RESTRICTION ENDONUCLEASE AND METHYLASE

BACKGROUND OF THE INVENTION

The present invention relates to clones for the HhaI restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al., *Gene* 3: 97-112, (1978); EcoRII: Kosykh et al., *Molec. gen. Genet.* 178: 717-719, (1980); PstI: Walder et al., *Proc. Nat. Acad. Sci.* U.S.A. 78 1503-1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E.coli* cloning plasmids (EcoRV: Bougueleret et al., *Nucleic Acids Res.* 12:3659-3676, (1984); PaeR7: Gingeras and Brooks, *Proc. Natl. Acad. Sci.* U.S.A. 80:402-406, (1983); Theriault and Roy, *Gene* 19:355-359, (1982); PvuII: Blumenthal et al., *J.Bacteriol.* 164:501-509, (1985)).

A third approach, and one that is being used to clone a growing number of systems, involves selecting for an active methylase gene referring to our Patent application No.: 707079 (BsuRI: Kiss et al., *Nucleic Acids Res.* 13:6403-6421, 1985). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., *Gene* 10:219-225, (1980); BcnI: Janulaitis et al., *Gene* 20: 197-204, (1982); BsuRI: Kiss and Baldauf, *Gene* 21: 111-119, (1983); and MspI: Walder et al., *J. Biol. Chem.* 258:1235-1241, (1983)).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease.

Another obstacle to cloning restriction-modification systems in *E.coli* was discovered in the process of cloning diverse methylase genes. Many *E.coli* strains (including those normally used in cloning) have systems that resist the introduction of DNA containing methylated cytosines. (Raleigh and Wilson, *Proc. Natl. Acad. Sci.* U.S.A. 83:9070-9074, (1986)). It is extremely difficult to clone cytosine-specific methylase genes, either alone, or together with their corresponding endonuclease gene, into these strains of *E.coli*. In order to clone these genes, therefore, it is necessary to use mutant strains of *E.coli* in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the HhaI restriction endonuclease and modification methylase derived from *Haemophilus haemolyticus* ATCC 10014, as well as related methods for the production of the enzymes. More specifically, this invention relates to clones which express the restriction endonuclease HhaI, an enzyme which recognizes the DNA sequence GCGC and cleaves between the 3' G and C residues. See Roberts, Myers, Morrison and Murray, *J. Mol. Biol.* 103: 199-208 (1976), the disclosure of which is hereby incorporated by reference herein. HhaI restriction endonuclease produced in accordance with the present invention is substantially pure and free of the contaminants normally found in HhaI preparations made by conventional techniques, such as that disclosed by Roberts et al., supra.

The preferred method for cloning this enzyme comprises forming a library containing the DNA from *Haemophilus haemolyticus*, isolating those clones which contain DNA coding for the HhaI modification methylase and screening among these to identify those that also contain the HhaI restriction endonuclease gene.

DETAILED DESCRIPTION OF THE INVENTION

The present invention relates to clones of the HhaI restriction and modification genes, as well to the restriction endonuclease HhaI produced from such clones. The HhaI genes are cloned by a method which takes advantage of the fact that certain clones which are selected on the basis of containing and expressing the HhaI modification methylase gene also contain the HhaI restriction gene. The DNA of such clones is resistant to digestion, in vitro, by the HhaI restriction endonuclease. This resistance to digestion affords a means for selectively isolating clones encoding the HhaI methylase and restriction endonuclease.

Figure 1:
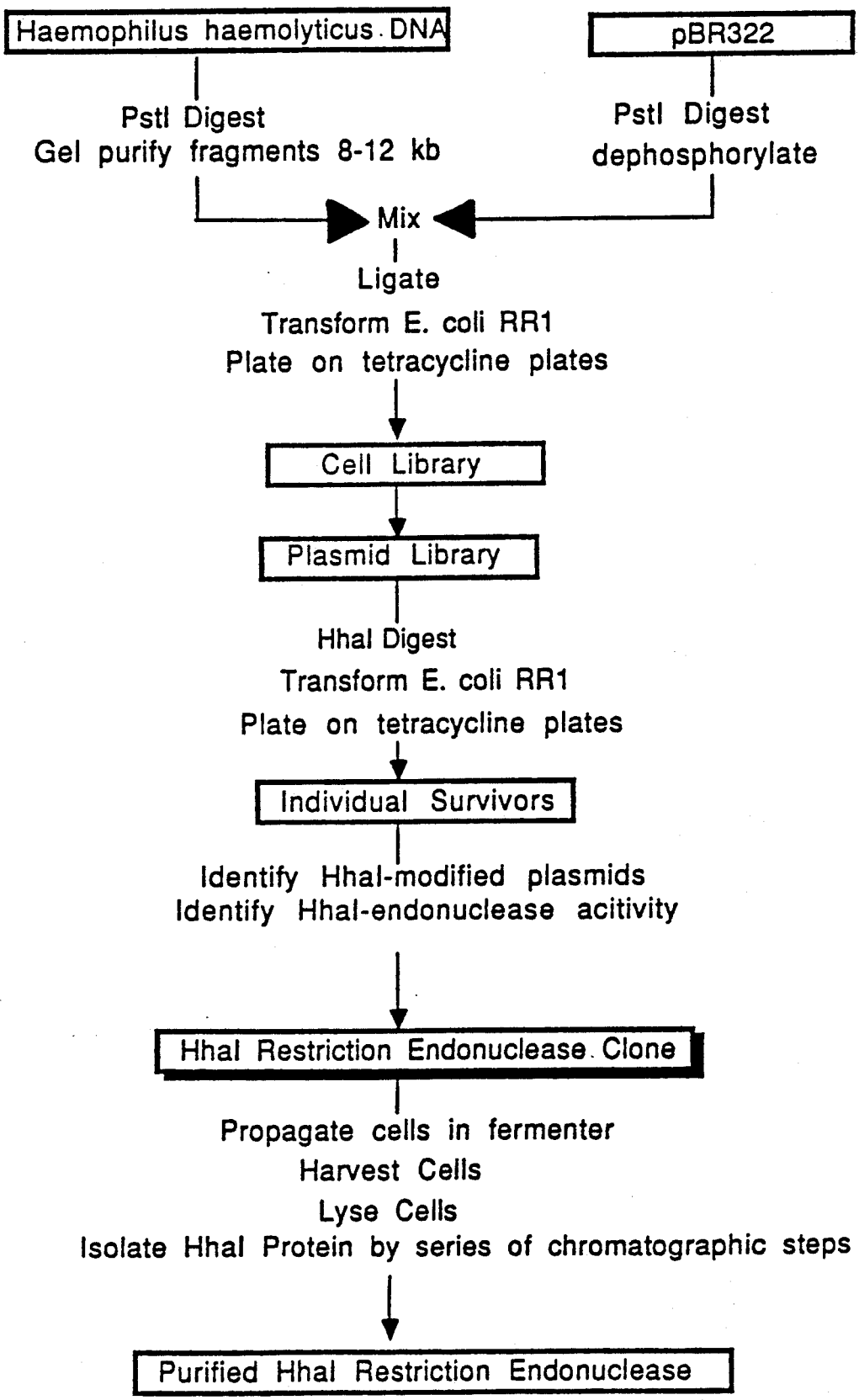
FIG. 1 illustrates the scheme for cloning and producing the HhaI restriction endonuclease.

The method described herein by which the HhaI restriction gene and methylase gene are preferably cloned and expressed are illustrated in FIG. 1, and they include the following steps:

1. The DNA of *Haemophilus haemolyticus* is purified. *Haemophilus haemolyticus* has been described in a number of publications including Roberts et al., supra. Samples of this bacterium are available from the American Type Culture Collection, catalog No. ATCC 10014.

2. The DNA is digested with the restriction endonuclease such a PstI.

3. The digested DNA is ligated to a cloning vector such as pBR322 (ATCC 37017) that contains one or more HhaI sites. The ligated DNA is transformed into an appropriate host such as *E.coli* strain RR1 (ATCC 31343).

4. The DNA/cell mixture is plated onto antibiotic media selective for transformed cells, such as tetracycline. After incubation, the transformed cell colonies are collected together into a single culture, the cell library.

5. The recombinant plasmids are purified in toto from the cell library to make the plasmid library.

6. The plasmid library is digested to completion with the HhaI restriction endonuclease, which can be prepared from *Haemophilus haemolyticus* by a method similar to that described in Roberts et al., supra. HhaI digestion differentially destroys unmodified, non-methylase-containing, clones, increasing the relative frequency of HhaI methylase-carrying clones.

7. The digested plasmid library DNA is transformed back into an appropriate host such as *E.coli* strain RR1, and transformed colonies are again obtained by plating on antibiotic plates. The colonies are picked and their DNA is analyzed for the presence of the HhaI modification gene in the following manner: The plasmid DNA that they carry is purified and incubated in vitro with HhaI restriction endonuclease to determine whether it is resistant to digestion by HhaI. The total cellular DNA (chromosomal and plasmid) of the clone is also purified and incubated with HhaI restriction endonuclease. The DNA of clones that carry the HhaI methylase gene should be fully modified, and both the plasmid DNA and the total DNA should be found to be substantially, or completely resistant to digestion.

8. Clones carrying the HhaI restriction endonuclease are identified by preparing crude extracts of those clones identified in step 7 as carrying the HhaI methylase gene, and assaying the extracts for HhaI restriction endonuclease activity.

9. The HhaI restriction endonuclease may be produced from clones carrying the HhaI restriction and modification genes by propagation in a fermenter in a rich medium containing tetracycline. The cells are thereafter harvested by centrifugation and disrupted by sonication to produce a crude cell extract containing the HhaI restriction endonuclease activity.

10. The crude cell extract containing the HhaI restriction endonuclease activity is purified by standard protein purification techniques such as affinity-chromatography and ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of HhaI Restriction Endonuclease Gene

1. DNA purification 10 g of frozen *Haemophilus haemolyticus* (ATCC 10014) cells were thawed on ice for 1 hour then resuspended in 20 ml of 25% sucrose, 50 mM Tris pH 8.0. 10 ml of 0.25M EDTA pH 8.0, and 6 ml of 10 mg/ml lysozyme in 0.25M Tris pH 8.0 were added. The suspension was kept on ice for 2 hours, then lysed by the addition of 24 ml of 1% Triton X-100, 50 mM Tris pH 8.0, 67 mM EDTA and 5 ml of 10% SDS. The solution was extracted with 70 ml of phenol, (previously equilibrated with 0.5M Tris pH 8.0), and 60 ml of chloroform. The emulsion was centrifuged at 10K rpm for 30 minutes and the viscous upper layer was withdrawn and dialyzed against four changes of 10 mM Tris pH 8.0, 1 mM EDTA. The dialyzed solution was then digested with RNase at a final concentration of 100 ug/ml for 1 hour at 37° C. The DNA was then precipitated by adding NaCl to a final concentration of 0.4M, overlaying with 0.55 volumes of isopropyl alcohol, and spooling the DNA onto a glass rod by mixing the phases together. The DNA was resuspended in DNA buffer (10 mM Tris pH 8.0, 1 mM EDTA) and stored at 4° C.

2. Digestion of DNA

The purified DNA was cleaved with PstI as follows: 100 ug of *H.haemolyticus* DNA in 1 ml of 10 mM Tris pH 7.5, 10 mM $MgCl_2$, 50 mM NaCl, 10 mM mercaptoethanol was digested with 1000 units of PstI restriction endonuclease. The tube was incubated for 1 hour at 37° C. then heated for 15 minutes at 72° C. to stop the reaction. Earlier experimentation, involving hybridization of a clone carrying a 1.4 kb HindIII fragment coding for the HhaI modification methylase (Caserta et al., *J. Biol. Chem.* 262: 4770-4777 (1987)), established that the homologous PstI fragment that we sought to clone was approximately 9 kb in length. To simplify the cloning of this fragment, the PstI digested *H.haemolyticus* DNA was size-fractionated prior to ligation and a fraction containing fragments in the size range of 8-12 kb was purified. Fractionation was achieved by gel electrophoresis and extraction as follows: A 1.0% tris-acetate agarose gel was poured containing a trough for loading a bulk DNA restriction endonuclease digest. The gel was run overnight, at 20 milliamps to separate the bands in the region of 8-12 kb. The bands in the gel were visualized with long-wave UV light and the bands in the region of 8-12 kb were cut out of the gel and transferred to a syringe. The gel was extruded through an 18 gauge needle into a 50 ml centrifuge tube containing 1 ml of TAE. The slurry was centrifuged at 15000 rpm for 30 minutes at 4° C. in a Beckman J2-21 centrifuge. The DNA in the supernatant was precipitated with 2 volumes of isopropanol and resuspended in 100 ul of DNA buffer.

3. Ligation and transformation 1 ug (10 ul) of the size-fractionated DNA was mixed with 2 ug (20 ul) of PstI-cleaved and dephosphorylated pBR322 (ATCC 37017). 10 ul of 500 mM Tris pH 7.5, 100 mM $MgCl_2$, 100 mM DTT, 5 mM ATP, and 56.6 ul of sterile distilled water were added to bring the volume to 100 ul. 3.4 ul of T4 DNA ligase was added and the solution was incubated at 16° C. for 4 hours, then sterilized by extraction with 20 ul of chloroform. 80 ul of the ligated mixture was mixed with 1.0 ml of 50 mM NaCl, 5 mM $Na_3$Citrate, 67 mM $CaCl_2$ and 2.0 ml of ice-cold, competent *E.coli* RR1 (ATCC 31343) cells were added. The solution was incubated at 42° C. for 5 mins, then 8 ml of Luria-broth (L-broth) was added and incubation was continued a 37° C. for 4 hours.

4. Cell Library

The transformed cell culture was briefly centrifuged, the supernatant was discarded and the cells were resuspended in 1.0 ml of L-broth. 200 ul portions were plated onto Luria-agar (L-agar) plates containing 30 ug/ml tetracycline. After overnight incubation at 37° C., the plates were each flooded with 2.5 ml of 10 mM Tris pH 7.5, 10 mM $MgCl_2$ and the transformed colonies were scraped together and pooled.

5. Plasmid Library 2.5 ml of the cell library was inoculated into 500 ml of L-broth containing 30 ug/ml tetracycline. The culture was shaken overnight at 37° C. then centrifuged at 4000 rpm for 5 minutes. The supernatant was discarded and the cell pellet was resuspended in 10 ml of 25% sucrose, 50 mM Tris pH 8.0, at room temperature. 5 ml of 0.25M EDTA, pH 8.0, and 3 ml of 10 mg/ml lysozyme in 0.25M Tris, pH 8.0 were added. The solution was left on ice for 1 hour, then 12 ml of 1% Triton X-100, 50 mM Tris pH 8.0, 67 mM EDTA was forcefully pipetted in, and the suspension was gently swirled to achieve lysis.

The lysed mixture was transferred to a 50 ml tube and centrifuged for 45 min. at 17000 rpm, 4° C. The supernatant was removed with a pipette. 20.0 gm of solid CsCl was weighed into a 50 ml plastic screw-cap tube and 22.0 gm of supernatant was pipetted into the tube and mixed. 1.0 ml of 5 mg/ml ethidium bromide in 10 mM Tris pH 8.0, 100 mM NaCl, 1 mM EDTA was added. The solution was transferred to two ⅝ in.×3 in. centrifuge tubes and spun in a Beckman Ti70 rotor for 42 hours at 44000 rpm, 17° C. To collect the plasmids, the tubes were opened, illuminated with ultraviolet light, and the lower of the two fluorescent bands was collected by syringe. The lower band from each tube was combined and the ethidium bromide was removed by extracting four times with an equal volume of water-saturated, ice-cold N-Butanol.

The extracted solution was dialyzed against 4 changes of 10 mM Tris pH 7.5, 1 mM EDTA, then the nucleic acid was precipitated by the addition of 2 vols. of isopropanol and sufficient 5M NaCl to reach a final concentration of 0.4M. The solution was stored overnight at −20° C. then centrifuged for 15 min. at 15000 rpm, 0° C. The supernatant was discarded, the pellet was air-dried for 15 min. then dissolved in 500 ul of 10 mM Tris pH 7.5, 1 mM EDTA and stored at −20° C. The plasmid DNA concentration was found to be approximately 150 ug/ml.

6. Digestion of the Plasmid Library

The primary plasmid library was digested with serial dilutions of HhaI endonuclease at the following concentrations: 5, 2.5, 1.3 and 0.6 units of HhaI endonuclease per ug of plasmid DNA. The tubes were incubated for 37° C. for 1 hour. The reaction was terminated by heating to 72° C. for 10 minutes.

7. Transformation 10 ul of the digests were transformed into *E.coli* RR1, plated onto L-agar containing 30 ug/ml tetracycline and incubated overnight at 37° C. A total of 132 colonies grew on the plate selected with 2.5 units of HhaI per ug of DNA; these were picked and screened to identify those that had incorporated the 9 kb fragment carrying the HhaI methylase gene.

8. Analysis of surviving individuals

The 132 colonies were streaked onto two plates, one containing ampicillin and the other containing tetracycline. 28 of 132 colonies were ampicillin-sensitive suggesting that they had incorporated fragments of DNA. The plasmids carried by these clones were purified by the plasmid miniprep procedure of Birnboim and Doly, *Nucleic Acids Res.* 7:1413(1979).

Miniprep Procedure

Each culture was centrifuged at 8000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 ul of 10 mM Tris, 1 mM EDTA, pH 8.0. 75 ul of 5M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10 mM Tris, 1 mM EDTA, pH 8.0, containing 100 ug/ml RNase and incubated for 1 hour at 37° C. to digest the RNA. The DNA was precipitated once more by the addition of 50 ul of 5M NaCl followed by 350 ul of isopropanol. After 10 minutes at room temperature, the DNA was spun down by centrifugation for 45 seconds, the supernatants were discarded and the pellets were redissolved in 150 ul of 10 mM Tris 1 mM EDTA, pH 8.0. The plasmid minipreps were subsequently analyzed by digestion with HhaI and PstI.

9. HhaI Methylase Gene Clone

Figure 2:
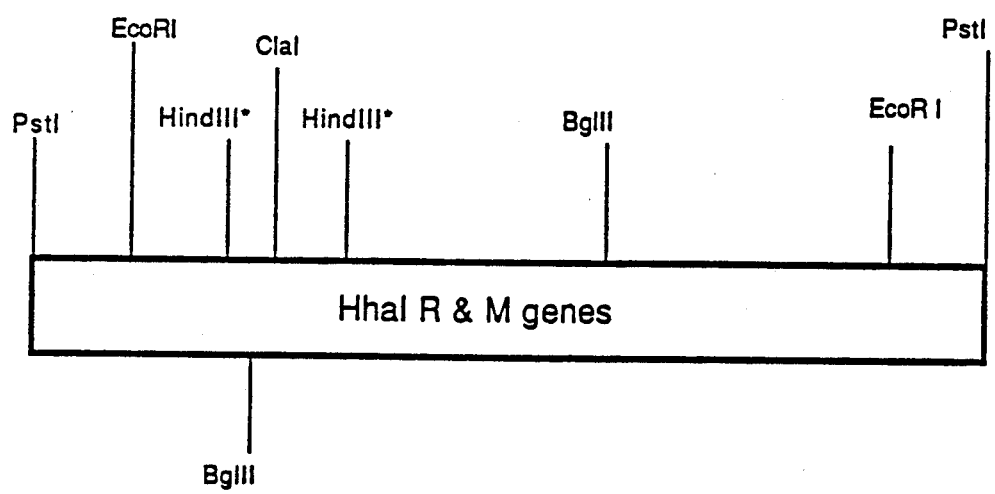
FIG. 2 is a restriction map of a 9 kb PstI fragment of *H.haemolyticus* DNA that encodes the HhaI restriction endonuclease and modification methylase. The fragment was ligated into the Pst site of pBR322 (ATCC 37017) to create pJB1394-2.

One clone of the 28 analyzed, pJB139RM 4-2, contained the 9 kb fragment; it was resistant to HhaI digestion, and it hybridized to the 1.4 kb HindIII fragment carrying the HhaI methylase gene. This plasmid was subsequently shown to carry not only the HhaI methylase gene but also the HhaI endonuclease gene (FIG. 2). A sample of pJB139RM 4-2 has been deposited at the American Type Culture Collection under ATCC Accession No. 40872.

10. HhaI Restriction Gene Clone

The clone identified above (section 9) as carrying the HhaI modification methylase gene was also found to carry the HhaI restriction endonuclease gene. This was established by in vitro restriction endonuclease assays performed as follows:

Endonuclease Assay

To assay for HhaI endonuclease activity, two solutions were prepared:
(i) 10X restriction endonuclease buffer: 100 mM Tris, pH 7.5, 100 mM $MgCl_2$, 60 mM mercaptoethanol, 200 mM KCl.
(ii) digestion reaction mix: 18 ul lambda DNA (630 ug/ml), 56 ul 10X restriction endonuclease buffer, 486 ul distilled water The cell extract was prepared as follows: A 50 ml culture was grown overnight in L-broth plus 30 ug/ml tetracycline at 37° C. The cells were pelleted by centrifugation at 4000 rpm for 5 minutes then resuspended in 3 ml of 10 mM Tris pH 8.0, 10 mM mercaptoethanol, 0.1 mM EDTA. 0.5 ml of 10 mg/ml lysozyme in the same buffer was added and the suspension was left on ice for 3 hours. The suspension was placed at $-20°$ C. overnight and thawed on ice. A 1 ml sample was transferred to an Eppendorf tube and made 0.005% Triton X-100, mixed and centrifuged for 10 minutes in an Eppendorf centrifuge at 4° C. The supernatant was used as the cell extract. To assay the extract, the digestion reaction mix was dispensed into 4 tubes, 150 ul into the first tube and 102.5 ul into each of the remaining 4 tubes. 7.5 ul of the extract was added to the first tube and mixed. 47.5 ul was removed from the first tube and transferred to the second tube, mixed and so on. The first tube thus received 1 ul of extract per ug of DNA, the second tube 0.3 ul/ug, the third tube 0.1 ul/ug and so on. The tubes, each containing 100 ul, were incubated at 37° C. for one hour, then a 20 ul sample of each was analyzed by gel electrophoresis. The titre of the extract was found to be approximately $1 \times 10^4$ units per ml, which corresponds to about $5 \times 10^4$ units of HhaI restriction enzyme per gram of wet cell paste.

11. EcoRI-deletion and sub-cloning of pJB139RM 4-2

Figure 3:
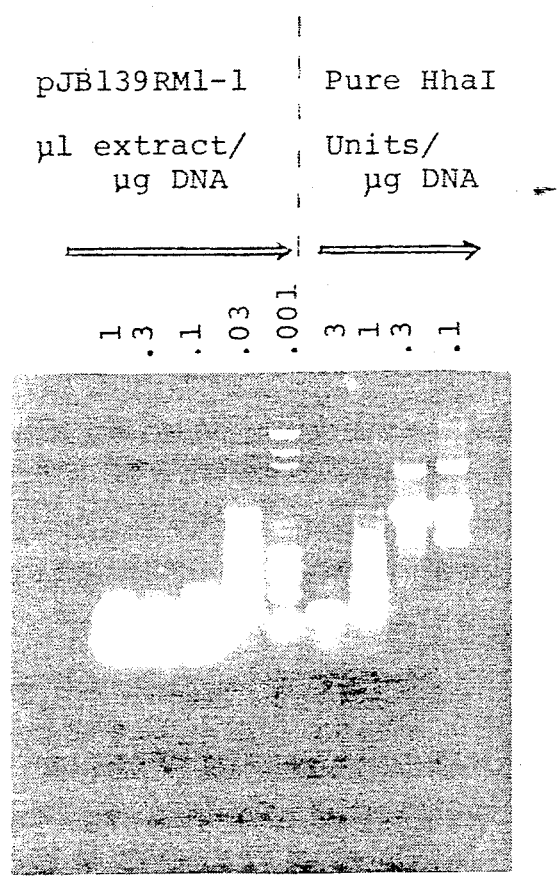
FIG. 3 is a photograph of an agarose gel illustrating HhaI restriction endonuclease activity in a crude cell extract of *E.coli* RR1 (ATCC 31343) carrying pJB139RM 4-2.

20 ug of purified pJB139RM 4-2 DNA was digested with 20 units of EcoRI restriction endonuclease in 100 ul of 10 mM Tris pH 7.5, 10 mM $MgCl_2$, 10 mM mercaptoethanol, 100 mM NaCl for 1 hour at 37° C. The digestion was electrophoresed on a 1% agarose gel and the 6 kb EcoRI fragment, internal to the 9 kb PstI fragment, was excised and purified (section 2). 1 ug of the 6 kb EcoRI fragment was ligated with 2 ug of EcoRI-cleaved and dephosphorylated pBR322 (section 3), transformed into competent *E.coli* RR1, and plated onto L-agar plates containing 100 ug/ml ampicillin. Fourteen colonies were picked and screened (section 8) to identify plasmids that had incorporated the 6 kb fragment. One of the fourteen analyzed appeared to contain the 6 kb fragment and was designated pJB139RM 1-1.

pJB139RM 1-1 was found to be fully HhaI-modified, indicating that, like the parent pJB139RM 4-2, it carried and expressed the HhaI methylase gene. Extracts of *E.coli* RR1 carrying pJB139RM 1-1 were found to contain approximately 5 times the level of HhaI endonuclease activity found in extracts of cells carrying pJB139RM 4-2, that is, approximately $5 \times 10^4$ units per ml of extract (FIG. 3). RR1 carrying pJB139RM 1-1 is the preferred strain from which the HhaI endonuclease can be purified.

What is claimed is:

1. Isolated DNA coding for the HhaI restriction endonuclease, wherein the isolated DNA is obtainable from the vector pJB139RM 4-2.

2. A recombinant DNA vector comprising a vector into which a DNA segment coding for the HhaI endonuclease produced by *Haemophilus haemolyticus* ATCC No. 10014 has been inserted.

3. Isolated DNA coding for the HhaI restriction endonuclease and methylase, wherein the isolated DNA is obtainable from the vector pJB139RM 4-2.

4. A cloning vector comprising the isolated RNA of claim 1.

5. A cloning vector comprising the isolated DNA of claim 3.

6. The cloning vector of claim 5, wherein the cloning vector comprises pJB139RM 4-2.

7. A host cell transformed by the vector of claim 4, 5 or 6.

8. A method of cloning DNA coding for an HhaI restriction endonuclease comprising:
   (a) purifying DNA from *Haemophilus haemolyticus* ATCC No. 10014;
   (b) digesting the purified DNA with PstI to form DNA fragments;
   (c) purifying, by gel electrophoresis, DNA fragments in the size range of 8–12 kb and isolating these DNA fragments;
   (d) ligating the DNA fragments of step (c) into a cloning vector containing one or more HhaI recognition sites or their equivalent;
   (e) transforming a host cell with the cloning vector of step (d) to form a cell library;
   (f) purifying recombinant vectors from the cell library to form a plasmid library;
   (g) contacting the plasmid library or step (f) with HhaI to form a digestion pool, transforming the digestion pool into a host cell, and screening for the presence of one or more cloning vectors containing DNA coding for an HhaI methylase;
   (h) screening the cloning vector of step (g) which contains DNA coding for an HhaI methylase for the presence of DNA coding for an HhaI restriction endonuclease; and
   (i) isolating the cloning vector of step (h) which contains DNA coding for HhaI restriction endonuclease.

9. A method of producing HhaI restriction endonuclease comprising culturing a host cell transformed with the vector of claim 4, 5 or 6 under conditions suitable for the expression of said endonuclease.

10. A method for producing HhaI restriction endonuclease comprising:
   (a) purifying DNA from *Haemophilus haemolyticus* ATCC No. 10014;
   (b) digesting the purified DNA with PstI to form DNA fragments;
   (c) purifying, by gel electrophoresis, DNA fragments in the size range of 8–12 kb and isolating these DNA fragments;
   (d) ligating the DNA fragments of step (c) into a cloning vector containing one or more HhaI recognition sites or their equivalents;
   (e) transforming a host cell with the cloning vector of step (d) to form a cell library;
   (f) purifying recombinant vectors from the cell library to form a plasmid library;
   (g) contacting the plasmid library or step (f) with HhaI to form a digestion pool, transforming the digestion pool into a host cell, and screening for the presence of one or more cloning vectors containing DNA coding for an HhaI methylase;
   (h) screening the cloning vector of step (g) which contains DNA coding for an HhaI methylase for the presence of DNA coding for an HhaI restriction endonuclease; and
   (i) isolating the cloning vector of step (h) which contains DNA coding for HhaI restriction endonuclease;
   (j) culturing a host cell transformed with the cloning vector of step (i) under conditions suitable for expression of HhaI restriction endonuclease.

* * * * *